United States Patent [19]

Stahel

[11] 4,299,994

[45] Nov. 10, 1981

[54] POLYOXYALKYLENE CONDENSATION PRODUCTS

[75] Inventor: Franklin H. Stahel, Mountain Lakes, N.J.

[73] Assignee: Sandoz, Inc., East Hanover, N.J.

[21] Appl. No.: 119,048

[22] Filed: Feb. 6, 1980

[51] Int. Cl.$^3$ ............................................. C07C 43/04
[52] U.S. Cl. ..................................... 568/625; 252/8.9; 252/170; 252/351; 252/352; 252/DIG. 1; 8/137; 8/609
[58] Field of Search ......................................... 568/625

[56] References Cited

U.S. PATENT DOCUMENTS 3,956,401  5/1976  Scardera et al. .................... 568/625

FOREIGN PATENT DOCUMENTS 2448388  4/1975  Fed. Rep. of Germany ...... 568/622

*Primary Examiner*—Howard T. Mars
*Attorney, Agent, or Firm*—Gerald D. Sharkin; Richard E. Vila; Joseph J. Borovian

[57] ABSTRACT

The invention relates to novel, polyoxyalkylene condensation products based on mixtures of primary, aliphatic alcohols, at least 70 mol % of which are branched 1-decanols, and to the use of these products as surface active agents.

10 Claims, No Drawings

POLYOXYALKYLENE CONDENSATION PRODUCTS

This invention relates to a new class of surface active agents. More particularly, it relates to novel, polyoxyalkylene condensation products based on mixtures of primary, aliphatic alcohols, at least 70 mol% of which are branched 1-decanols, and to the use of these products as surface active agents.

Synthetic surface active agents, e.g., detergents, can be characterized as compounds which incorporate within the molecular structure thereof a hydrophobic moiety, typically a long-chain alkyl moiety, and also a hydrophilic moiety which, because of being polar in character or having ionic charge, is capable of interaction with water molecules. When the hydrophilic moiety is characterized by a formal ionic charge, the surface active agent is classified as anionic or cationic, depending upon the nature of the ionic charge. Alternatively, if the hydrophilic moiety does not possess a formal ionic charge, the surface active agent is termed a non-ionic surface active agent. One frequently encountered class of non-ionic surface active agents comprises alkylene oxide derivatives of active hydrogen compounds, particularly the alkylene oxide derivatives of fatty acids or long-chain alcohols. However, since the available supply of natural fatty acids and alcohols does not always coincide with the demands of the surface active agent industry, such products are subject to extremely large price fluctuations and, as a consequence thereof, exhibit severe economic shortcomings. The dual problem of availability and price is particularly severe during periods of national emergency or war.

Simple condensation products of a single alkylene oxide, particularly ethylene oxide, and a higher alcohol are well known in the art. Of more recent importance are alkylene oxide derivatives of higher alcohols wherein the polyoxyalkylene portion incorporates more than one type of alkylene oxide, e.g., incorporates moieties of ethylene oxide and also moieties of propylene oxide. The presence of the propylene oxide or a higher alkylene oxide serves to modify and, in general, reduce the hydrophilic character of the alkylene oxide portion of the surfactant. For example, U.S Pat. No. 3,036,130 discloses alkoxylate derivatives of monohydric alcohols wherein a first alkylene oxide block is ethylene oxide and a second alkylene oxide block is propylene oxide. A similar disclosure is found in U.S. Pat. No. 2,677,700, except that in this earlier patent the first alkylene oxide block is propylene oxide and the second alkylene oxide block is ethylene oxide. A somewhat different type of derivative is disclosed in U.S. Pat. No. 3,101,374. There, lower alcohols were alkoxylated initially with ethylene oxide and propylene oxide and then with a mixture of ethylene oxide and propylene oxide to introduce a second block which was heteric, that is, consisted of a random mixture of ethylene oxide and propylene oxide.

Accordingly, it is an object of the present invention to provide a new class of polyoxyalkylene condensation products. It is another object of the present invention to provide new polyoxyalkylene condensation products which are useful as non-ionic surface active agents. It is still another object of the present invention to provide polyoxyalkylene condensation products which not only possess a wide range of surface active properties, but are also economically attractive.

The attainment of the above objects is made possible by mixtures of compounds of formula I:

$$R\text{-}(OC_3H_6)_{\overline{m}}(OC_2H_4)_{\overline{n}}OH \qquad I$$

wherein

R is the residue of a mixture of primary, aliphatic alcohols, at least 70 mol% of which is branched 1-decanols, the remaining components consisting essentially of primary, aliphatic alcohols having an average of 8 to 12 carbon atoms, m is 1 to 4, and n is 3 to 20.

Preferably, m is 1 to 3, more preferably 1 or 2.

Preferably, n is 3 to 15, more preferably 3–10, most preferably, 3 to 7.

Preferably, R is the residue of a mixture of primary, aliphatic alcohols, at least 90 mol% of which is branched 1-decanols.

Preferred mixtures of compounds of formula I are the mixtures of compounds of formula Ia:

$$R'\text{-}(OC_3H_6)_{\overline{m'}}(OC_2H_4)_{\overline{n'}}OH \qquad TM\ Ia$$

where

R' is the residue of a mixture of primary, aliphatic alcohols, at least 95 mol% of which is branched 1-decanols, m' is 1 to 3, and n' is 3 to 15.

The more preferred mixtures of compounds of formula I are the mixtures of compounds of formula Ib:

$$R''\text{-}(OC_3H_6)_{\overline{m''}}(OC_2H_4)_{\overline{n''}}OH \qquad Ib$$

where

R'' is the residue of a mixture of primary, aliphatic, branched 1-decanols, especially such mixtures, the major isomers of which are trimethyl-1-heptanols, m'' is 1 or 2, and n'' is 3 to 10.

The even more preferred mixtures are those of compounds of formula Ib wherein R'' and m'' are as defined above and n'' is 3 to 7.

The most preferred mixture is the mixture of compounds of formula Ib wherein R'' is the residue of a mixture of primary, aliphatic branched 1-decanols, the major isomers of which are trimethyl-1-heptanols, m'' is 1.5 and n'' is 5.

The compounds of formula I are produced by more or less conventional methods which can best be illustrated by the following reaction scheme:

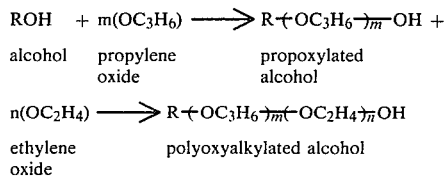

```
ROH      + m(OC3H6) ——> R-(OC3H6)m̄-OH +
alcohol    propylene         propoxylated
           oxide              alcohol n(OC2H4) ——> R-(OC3H6)m̄-(OC2H4)n̄-OH
ethylene          polyoxyalkylated alcohol
oxide
``` where R is as defined above and m and n are the moles of propylene oxide and ethylene oxide, respectively. Suitable results are obtained by adding to the alcohol to be alkoxylated a catalytic amount, e.g., from about 0.2% to 1%, preferably, 0.3% to 0.75%, by weight of the total amount of reactants, including the propylene oxide and ethylene oxide, of an alkaline catalyst. Catalysts which may be employed include alkali metal hydroxides, sodium ethylate, sodium methylate, alkali metal acetates and dimethylamine, or a mixture thereof. Preferred catalysts are the alkali metal hydroxides, more preferably, sodium hydroxide or potassium hydroxide. Any other types of catalysts commonly used for alkylene oxide condensation reactions may also be employed.

Although optional, it is preferred to additionally add to the alcohol to be alkoxylated, a small amount of a reducing agent to minimize discoloration of the resulting polyalkoxylated alcohol. Suitable reducing agents which may be employed include sodium borohydride, lithium aluminum hydride, diborane and the like, preferably, sodium borohydride.

An amount of propylene oxide calculated to provide the desired degree of propoxylation is then introduced and the resulting mixture is allowed to react until the propylene oxide is consumed, as indicated by a drop in reaction pressure. A similar introduction and reaction of a calculated amount of ethylene oxide serves to provide the second block which completes the alkoxylation. Customarily, the alkoxylated product is finally treated with weak acid, e.g., glacial acetic acid, to neutralize any basic catalyst residues.

It should be understood that each separate alkoxylation procedure serves to introduce a desired average number of alkylene oxide units per alcohol molecule. Thus, for example, the initial treatment of an alcohol mixture with m moles of propylene oxide per mole of alcohol serves to effect the propoxylation of each alcohol moiety with propylene oxide to an average of m propylene oxide moieties per alcohol moiety, although some alcohol moieties will have become combined with more than m propylene oxide moieties and some will have become combined with less than m. In general, the maximum number of propyleneoxy units in a single molecule will not exceed 8 and the number of ethyleneoxy units in a single molecule will not exceed 30. The variation in the number of alkylene oxide moieties is not critical as long as the average for the number of units in each block is within the limits set out for the m and n terms in formula I above, which terms, as average values, are other than whole numbers in some instances.

Each alkoxylation is conducted at an elevated temperature and pressure. Suitable reaction temperatures are from about 120° C. to about 220° C., preferably, 130° C. to 180° C. and, more preferably, 140° C. to 160° C. A suitable reaction pressure is achieved by introducing to the reaction vessel the required amount of propylene oxide or ethylene oxide, each of which has a high vapor pressure at the desired reaction temperature. The pressure serves as a measure of the degree of reaction and each alkoxylation is considered to be complete when the pressure no longer decreases with time.

For best results, it is desirable to carry out the alkoxylation under relatively moisture-free conditions and to avoid side reactions which form water. To dry the reaction vessel and connections, they may be swept out with dry, oxygen-free gas, e.g., nitrogen, before introducing the charge. The catalyst or catalyst mixture should also be dry, or substantially so. The propylene oxide and ethylene oxide should preferably be purified to remove moisture and any impurities which are capable of entering into side reactions which yield water.

The starting alcohols, i.e., the mixture of primary, aliphatic alcohols, are known. For example, they may be prepared by the well known "oxo" process comprising reacting a mixture of olefins, the predominant components of which have 9 carbon atoms, with carbon monoxide and hydrogen. The reaction can be carried out to produce aldehydes, which aldehydes are subsequently hydrogenated to alcohols, or can be conducted as a hydroformylation reaction in which the aldehydes initially formed are simultaneously hydrogenated and converted to saturated, primary, aliphatic alcohols having predominantly 10 carbon atoms.

Suitable methods of producing oxo aldehydes which are hydrogenated to the desired alcohols are described, e.g., in U.S. Pat. No. 2,564,456 and U.S. Pat. No. 2,587,858. Generally, it is more advantageous to employ the hydroformylation method described above to produce the alcohol mixture directly; processes of this type are described in U.S. Pat. No. 2,504,682 and U.S. Pat. No. 2,581,988. The hydroformylation is suitably carried out in the presence of a hydrogenation catalyst, advantageously employing a temperature of about 200° C. to 400° C. under superatmospheric pressure, preferably at least 200 atmospheres, with a molar ratio of olefin to carbon monoxide to hydrogen in the range of from about 1:2:2 to about 1:5:20.

The novel, polyoxyalkylene condensation products of this invention are useful per se as surface active agents or as intermediates in the preparation of other surface active agents.

The uses to which surface active agents can be put are numerous and well known. Thus, the surface active agents of the present invention are suitable as detergents, wetting agents, dispersants, levelling agents, softening agents and the like in the detergent, textile, leather, paper, lacquer and rubber industries. For example, the novel, polyoxyalkylene condensation products may be employed in detergent compositions as the sole surfactant thereof or may also advantageously be employed in detergent compositions containing an anionic, nonionic, ampholytic or zwitterionic surfactant, or mixtures thereof, and/or builders and the like. As representative of anionic surfactants may be mentioned: (1) alkylbenzenesulfonates, such as sodium and potassium salts having a branched or straight chain alkyl portion of about 9 to about 15 carbon atoms; (2) alkyl sulfates, such as the sodium and triethanolammonium salts of $C_{10}$–$C_{20}$ alkyl sulfuric acid, prepared by sulfating the alcohols derived from coconut oil or tallow, or prepared synthetically; (3) the alkali metal and ammonium salts of the sulfated ethoxylates of a long-chain alcohol and 3 to 5 molar proportions of ethylene oxide, e.g., the ammonium salt of an ethoxylate containing an average of 3.1 molar proportions of ethylene oxide and 1 mole of an alcohol mixture known commercially as ALFOL 1412, composed of about ⅔ n-tetradecanol and about ⅓ n-dodecanol; (4) the compounds known as "Medialans" which are amido carboxylic acids formed by condensing fatty acids of $C_8$–$C_{22}$ chain length with sarcosine, $CH_3NHCH_2COOH$; (5) alkanesulfonates, such as ammonium dodecanesulfonate; (6) alkoxyhydroxypropanesulfonates, such as the water-soluble salts of 3-dodecyloxy-2-hydroxy-1-propane-sulfonate; (7) soaps, the surface-active substances formed usually by the reaction of caustic alkalies with natural glyceridic fats and oils, generally prepared in high purity, and having the generic molecular formula RCOONa, wherein R is a straight-chain hydrocarbon group having from about 7 to about 21 carbon atoms; and (8) olefin sulfonates, such as dodecene sulfonate, and the compounds described in U.S. Pat. No. 3,332,880. As representative of non-ionic surfactants may be mentioned: (1) the Pluronics, formed by condensing propylene oxide with propylene glycol to a molecular weight of about 600 to 2500 to form a base followed by condensing ethylene oxide to this base to the extent of about 10 to about 90 percent, total molecule basis. U.S. Pat. No. 2,674,619 and U.S. Pat. No. 2,677,700 describe operable compounds; (2) compounds formed by the simultaneous polymerization of propylene oxide and ethylene oxide, and containing randomly positioned oxypropylene and oxyethylene groups. These and related compounds are described in U.S. Pat. No. 2,979,528, U.S. Pat. No. 3,036,118, U.S. Pat. No. 3,022,335, U.S. Pat. No. 3,036,130 and U.S. Pat. No. 3,048,548; (3) alkyl phenols having 9 to 12 carbon atoms in the alkyl portion (straight or branched) ethoxylated with 4–10 molar proportions of ethylene oxide; and (4) ethoxylates of fatty alcohols having 8 to 18 carbon atoms per molecule and 5-30 molar proportions of oxyethylene groups.

As an example of an ampholytic surfactant may be mentioned the hydroxyalkyl methyl taurates, while cocodimethyl sulfopropyl betaine is exemplary of a zwitterionic surfactant.

Other common components of detergent compositions include alkaline builders such as the alkali metal salts of ortho-, meta-, poly- and pyro-phosphoric acids, including sodium hexametaphosphate, sodium pyrophosphate, trisodium phosphate, sodium tripolyphosphate, and the like, in addition to water-soluble derivatives of high polyoses such as sodium carboxymethyl cellulose, and other water-soluble salts for adjustment of pH, buffering, and the like such as sodium carbonate, sodium sesquicarbonate, sodium bicarbonate, sodium chloride, sodium sulfate, sodium bisulfate, sodium metasilicate, and the like.

The following examples, illustrating the novel polyoxyalkylene condensation products of this invention, are presented without any intention that the invention be limited thereto. All parts and percentages are by weight.

EXAMPLE 1

To a reaction vessel are added, with stirring, 705.0 g. of decyl alcohol (a mixture of primary, aliphatic alcohols, at least 90 mol% of which is branched 1-decanols, a boiling range of 216° C. to 223° C., a specific gravity @ 20/20° C. of 0.838, a refractive index, $n_D^{20}$, of 1.440, a pour point of $-65°$ F., a viscosity @ 20° C. of 22.5 centistokes and a solubility in water @ 20° C. of <0.05 g./100 g. and available commercially from Exxon Chemical Co.), 10.6 g. of potassium hydroxide (in pellet form) and 0.12 g. of sodium borohydride. After heating the reaction mixture to 60° C. under 30 inches of vacuum (equivalent to 5–10 mm. of mercury), the system is purged with nitrogen to break the vacuum and the purging procedure is repeated two additional times to minimize the presence of air. While maintaining the temperature of the reaction mixture at 60° C. and the vacuum of the reactive system at 30 inches for thirty minutes, a dropping funnel containing 260.0 g. of propylene oxide under vacuum is purged with nitrogen to break the vacuum and the purging procedure is repeated two additional times. The temperature of the reaction mixture is then raised to 100° C., at which time the addition of propylene oxide to the reaction mixture commences, which effects a lowering of the vacuum of the reaction system to 15 inches. Over a period of sixty minutes, the remaining propylene oxide is added, while the temperature of the resulting reaction mixture slowly rises to 155° C. and the vacuum of the resulting reaction system slowly decreases to 9 inches. After allowing the reaction mixture to react further until the vacuum of the reaction system rises to 30 inches, the procedure described above is repeated with an additional 257.0 g. of propylene oxide, which is added over a period of sixty minutes as the vacuum of the reaction system slowly decreases to 8 inches. After allowing the propoxylated alcohol reaction mixture to react further until the vacuum of the reaction system rises to 30 inches, the procedure described above is repeated with 1178.0 g. of ethylene oxide, which is added over a period of sixty minutes as the vacuum of the reaction system slowly decreases. After allowing the polyalkoxylated alcohol mixture to react further until the vacuum of the reaction system rises to 30 inches, the reaction system is purged with nitrogen to break the vacuum, the temperature of the system is cooled to 85° C. and an additional 0.12 g. of sodium borohydride is added to the polyalkoxylated alcohol mixture. The reaction system is then kept under a nitrogen atmosphere for 2 hours, while the temperature is maintained between 85° and 90° C. After neutralizing the catalyst present with glacial acetic acid, filtering of the insoluble materials yields a translucent, pale yellow liquid of the formula

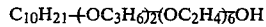

having a molecular weight of 490.8 and a hydroxyl number of 114.3.

EXAMPLE 2

Following essentially the procedure of Example 1 and employing the starting alcohol utilized in Example 1, i.e., the decyl alcohol available commercially from Exxon Chemical Co., and the appropriate amounts of propylene oxide and ethylene oxide, the following compounds are obtained:

(a) 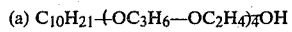

which is a translucent, pale yellow liquid having a molecular weight of 366.2 and a hydroxyl number of 153.2;

(b) 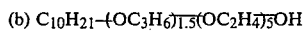

which is a translucent, pale yellow liquid having a molecular weight of 432.2 and a hydroxyl number of 129.8; and (c) 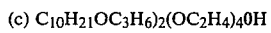

which is a translucent, pale yellow liquid having a molecular weight of 435.9 and a hydroxyl number of 128.7.

It should be understood that in Examples 1, 2(a), 2(b) and 2(c), the term "$C_{10}H_{21}$" refers to a mixture of primary, aliphatic alcohols, at least 90 mol% of which is branched 1-decanols, and the indicated number of propyleneoxy units and ethyleneoxy units are average values.

EXAMPLE 3

The following represent typical formulations useful as detergent compositions:

| Solid |
| --- |

-continued

|  | Percent | | | |
| --- | --- | --- | --- | --- |
|  | A | B | C | D |
| Example 1 compound | 17 | — | — | — |
| Example 2(a) compound | — | 17 | — | — |
| Example 2(b) compound | — | — | 17 | — |
| Example 2(c) compound | — | — | — | 17 |
| sodium tripolyphosphate | 50 | 50 | 50 | 50 |
| sodium silicate (Na$_2$O:SiO$_2$ = 1:2.5) | 6 | 6 | 6 | 6 |
| sodium toluene sulfonate | 2 | 2 | 2 | 2 |
| sodium carboxymethylcellulose | 0.3 | 0.3 | 0.3 | 0.3 |
| sodium sulfate | 13 | 13 | 13 | 13 |
| fluorescent dye | 0.16 | 0.16 | 0.16 | 0.16 |
| water | 8 | 8 | 8 | 8 |
| miscellaneous | balance | → | → | → |

Liquid

|  | Percent | | | |
| --- | --- | --- | --- | --- |
|  | A | B | C | D |
| Example 1 compound | 12 | — | — | — |
| Example 2(a) compound | — | 12 | — | — |
| Example 2(b) compound | — | — | 12 | — |
| Example 2(c) compound | — | — | — | 12 |
| tetrapotassium pyrophosphate | 19 | 19 | 19 | 19 |
| sodium silicate (Na$_2$O:SiO$_2$ = 1:1.6) | 3.8 | 3.8 | 3.8 | 3.8 |
| potassium toluene sulfonate | 8.5 | 8.5 | 8.5 | 8.5 |
| sodium carboxymethylcellulose | 0.3 | 0.3 | 0.3 | 0.3 |
| perfume | 0.2 | 0.2 | 0.2 | 0.2 |
| water | 56.2 | 56.2 | 56.2 | 56.2 |

What is claimed is:

1. A mixture of compounds of formula I, $$R\text{-}(OC_3H_6)_{\overline{m}}(OC_2H_4)_{\overline{n}}OH \qquad I$$

wherein
R is the residue of a mixture of primary, aliphatic alcohols, at least 70 mol% of which is branched 1-decanols, the remaining components consisting essentially of primary, aliphatic alcohols having an average of 8 to 12 carbon atoms,
m is 1 to 4, and
n is 3 to 20.

2. A mixture of compounds according to claim 1 wherein R is the residue of a mixture of primary, aliphatic alcohols, at least 90 mol% of which is branched 1-decanols.

3. A mixture of compounds according to claim 2 of formula Ia, $$R'\text{-}(OC_3H_6)_{\overline{m'}}(OC_2H_4)_{\overline{n'}}OH \qquad Ia$$

where
R' is the residue of a mixture of primary, aliphatic alcohols, at least 95 mol% of which is branched 1-decanols,
m' is 1 to 3, and
n' is 3 to 15.

4. A mixture of compounds according to claim 3 of formula Ib, $$R''\text{-}(OC_3H_6)_{\overline{m''}}(OC_2H_4)_{\overline{n''}}OH \qquad Ib$$

where
R'' is the residue of a mixture of primary, aliphatic, branched 1-decanols,
m'' is 1 or 2, and
n'' is 3 to 10.

5. A mixture of compounds according to claim 4 wherein the major isomers of R'' are trimethyl-1-heptanols.

6. A mixture of compounds according to claim 4 wherein n'' is 3 to 7.

7. A mixture of compounds according to claim 3 of the formula $$R'\text{-}(OC_3H_6)_{\overline{1.5}}(OC_2H_4)_{\overline{5}}OH$$

where R' is as defined in claim 3.

8. A mixture of compounds according to claim 3 of the formula $$R'\text{-}(OC_3H_6)(OC_2H_4)_{\overline{4}}OH$$

where R' is as defined in claim 3.

9. A mixture of compounds according to claim 3 of the formula $$R'\text{-}(OC_3H_6)_{\overline{2}}(OC_2H_4)_{\overline{4}}OH$$

where R' is as defined in claim 3.

10. A mixture of compounds according to claim 3 of the formula $$R'\text{-}(OC_3H_6)_{\overline{2}}(OC_2H_4)_{\overline{6}}OH$$

where R' is as defined in claim 3.

* * * * *

UNITED STATES PATENT AND TRADEMARK OFFICE
CERTIFICATE OF CORRECTION

PATENT NO. : 4,299,994
DATED : November 10, 1981
INVENTOR(S) : Franklin H. Stahel It is certified that error appears in the above—identified patent and that said Letters Patent is hereby corrected as shown below:

Column 2, directly beneath line 21; delete the formula "$R'\text{-}(OC_3H_6)_m\text{-}(OC_2H_4)_n\text{-}OH$ TM 1a" and substitute therefor -- $R'\text{---}(OC_3H_6)_{m'}\text{---}(OC_2H_4)_{n'}\text{---}OH$    Ia --.

Column 6, directly beneath line 40; delete the formula " (a) $C_{10}H_{21}\text{---}(OC_3H_6\text{---}OC_2H_4)_4\text{---}OH$ " and substitute therefor -- a) $C_{10}H_{21}\text{---}OC_3H_6\text{---}(OC_2H_4)_4\text{---}OH$ --.

Column 6, directly beneath line 50; delete the formula "(c) $C_{10}H_{21}OC_3H_6)_2(OC_2H_4)_4OH$" and substitute therefor -- c) $C_{10}H_{21}\text{---}(OC_3H_6)_2\text{---}(OC_2H_4)_4\text{---}OH$ --.

Column 8, directly beneath line 30; delete the formula " $R'\text{---}(OC_3H_6OC_2H_4)_4\text{---}OH$ " and substitute therefor -- $R'\text{---}OC_3H_6\text{---}(OC_2H_4)_4\text{---}OH$ --.

Signed and Sealed this

Fifteenth Day of March 1983

[SEAL]

Attest:

GERALD J. MOSSINGHOFF

Attesting Officer

Commissioner of Patents and Trademarks